US00PP27573P3

(12) United States Plant Patent
Olesen

(10) Patent No.: US PP27,573 P3
(45) Date of Patent: Jan. 24, 2017

(54) GROUND COVER ROSE PLANT NAMED 'POULTC019'

(50) Latin Name: ***Rosa* hybrid**
Varietal Denomination: Poultc019

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 124 days.

(21) Appl. No.: 14/121,286

(22) Filed: Aug. 15, 2014

(65) Prior Publication Data

US 2016/0050817 P1 Feb. 18, 2016

(51) Int. Cl.
*A01H 5/02* (2006.01)

(52) U.S. Cl.
USPC ..... Plt./101

(58) Field of Classification Search
USPC ..... Plt./101, 102
See application file for complete search history.

(56) References Cited

PUBLICATIONS

Poulsen Roser A/S—"Pagode-Perfection by Poulsen," Main Varieties 2013, retrieved off the internet Feb. 3, 2016 (1 page).*

* cited by examiner

*Primary Examiner* — Susan McCormick Ewoldt

(57) ABSTRACT

A new garden rose plant of the Ground Cover class which has abundant, orange red flowers and attractive foliage. This new and distinct variety has shown to be uniform and stable in the resulting generations from asexual propagation.

1 Drawing Sheet

Botanical designation: *Rosa* hybrid.
Variety denomination: 'Poultc019'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2003 and the resulting seeds were planted in a controlled environment in Fredensborg, Denmark. The new variety, named 'Poultc019', originated as a single seedling from the stated cross.

The new variety may be distinguished from its male pollen parent and female seed parent by the following characteristics. The female seed parent has medium yellow flowers, while the new variety has orange red flowers. The male pollen parent has flowers with 7-10 petals while the new variety has flowers with 20 petals.

The objective of the hybridization of this rose variety was to create a new and distinct variety for garden use with unique qualities, such as:

1. Uniform and abundant orange red flowers.
2. Vigorous, but compact growth when propagated both as a budded rose and on its own roots.
3. Exceptional disease resistance.

This combination of qualities is not present in previously available commercial cultivars of this type, known to the inventor, and distinguish 'Poultc019' from all other varieties of which we are aware.

As part of the rose development program, Mogens N. Olesen germinated the seeds from the aforementioned hybridization during winter of 2003 and conducted evaluations on the resulting seedlings in a controlled environment in Fredensborg, Denmark. 'Poultc019' was selected in the spring of 2004 by the inventor as a single plant from the progeny of the aforementioned hybridization.

Asexual reproduction of 'Poultc019' by traditional budding and rooted cuttings was first done by Mogens N. Olesen in the nursery in Fredensborg, Denmark in July, 2004. This initial and other subsequent asexual propagations conducted in controlled environments have demonstrated that the characteristics of 'Poultc019' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poultc019'.

Specifically illustrated in the drawing are flowers at various stages of development, flower in parts, leaves, and stems, and an inflorescence. Plants shown are 2 years of age.

DETAILED DESCRIPTION OF THE VARIETY

The following is a description of 'Poultc019', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulharmu', U.S. Plant Pat. No. 12,681 are compared to 'Poultc019' in Chart 1.

CHART 1

| | 'Poultc019' | 'Poulharmu' |
|---|---|---|
| Petal Count | 20 | 14-16 |
| Flower Diameter | 45 mm | 45 mm |
| General Tonality of Flower Color | Red Group 40A | Red Group 44B |

Flower and Flower Bud

Blooming habit: Continuous.

Flower bud:

*Size.*—Upon opening, 20 mm in length from base of receptacle to end of bud. Bud diameter is 8 mm.

*Bud form.*—Urceolate.

*Bud color.*—As sepals divide petals are Red Group 52B.

*Sepal inner surface.*—Color: Yellow-Green Group 148B. Surface: Lightly pubescent.

*Sepal outer surface.*—Color: Yellow-Green Group 144A with strong intonations of Greyed-Purple Group 185A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—18 mm long, 6 mm wide.

*Receptacle.*—Texture: Smooth. Size: 5 mm in height, 5 mm wide. Color: Yellow-Green Group 145B with intonations of Greyed-Red Group 181C. Shape: Campanulate.

*Pedicel.*—Surface: Small prickles. Length: 25 mm. Diameter: 2 mm on average. Color: Greyed-Red Group 179A. Strength: Moderate.

*Peduncle.*—Length: 5 to 3 cm. Diameter: About 3 mm. Color: Yellow-Green Group 144B. Texture: Smooth.

Flower bud development: Flower buds are normally borne in clusters of 3 to 5 flower buds per stem.

Flower bloom:

*Fragrance.*—Strong spicy scent.

*Duration.*—The blooms have a duration on the plant of approximately 10 days. Petals fall cleanly away from plant after flowers have fully matured.

*Size.*—Flower diameter is 45 mm when open. Flower depth is 17 mm.

*Flower shape.*—Open cup semi-double flower, with petals that curve out from the center.

Petalage: Under normal conditions, flowers have 20 petals total, about 3 of which are petaloids.

General tonality of flower: Open flowers are Red Group 40A.

Petal color:

*Upon opening.*—Upper surface: Red Group 40A with occasional streaks of Yellow Group 13B. Lower surface: Red Group 43C.

*Basal petal spots, upon opening.*—Upper surface: Yellow Group 8A. Lower surface: Yellow Group 8C.

*After opening.*—Upper surface: Red Group 46D with apical intonations of Red Group 52A. Basal intonations of Orange Group 29A. Lower surface: Red Group 52B with intonations of Red Group 48D at the basal zone. Occasional streaks of Yellow Group 8D.

*Basal petal spots, after opening.*—Upper surface: Yellow Group 8A. Lower surface: Yellow Group 8C.

Petals:

*Petal reflex.*—Flat.

*Margin.*—Entire and uniform with a small point at the apex. Weak to no undulations.

*Shape.*—Generally deltoid. Apex shape: Rounded to flat. Base shape: Broadly acute.

*Size.*—About 25 mm (l)×25 mm (w).

*Texture.*—Smooth.

*Thickness.*—Average.

Petaloids:

*Size.*—20 mm (l) by 9 mm (w).

*Quantity.*—About 3.

*Shape.*—Crescent.

*Color.*—Upper surface: Red Group 46D with apical intonations of Red Group 52A. Basal intonations of Orange Group 29A. At the base of the petaloid Yellow Group 8A. Lower surface: Red Group 52B with intonations of Red Group 48D at the basal zone. Occasional streaks of Yellow Group 8D. Yellow Group 8C at the base of the petaloid.

Reproductive organs:

*Pollen.*—None observed.

*Anthers.*—Size: 2 mm in length. Color: Yellow Group 10B. Quantity: 30 on average.

*Filaments.*—Color: Yellow Group 13A. Length: 6 mm.

*Pistils.*—Length: 4 mm. Quantity: 15 on average.

*Stigmas.*—Color: Yellow-Green Group 145D.

*Styles.*—Color: Green-White Group 157A.

*Location of stigmas.*—Inferior in location relative to the length of the filaments and the height of the anthers.

*Hips.*—None Observed.

Plant

Plant growth: Upright, bushy, compact. Plants are 45 cm in height, and 45 cm wide.

Stems:

*Color.*—Juvenile growth: Yellow-Green Group 144C with intonations of Greyed-Red Group 179B. Mature growth: Yellow-Green Group 144B.

*Length.*—On average, canes are 25 cm from the base of the plant to the flowering portion.

*Diameter.*—4 mm.

*Internodes.*—On mature canes, there is an average distance of 20 mm between nodes.

*Surface texture.*—Young wood: Smooth. Older wood: Smooth.

Long prickles:

*Incidence.*—9 prickles per 10 cm of stem.

*Size.*—Average length of prickles on mature stems is 7 mm.

*Shape.*—Upper portion is linear. Lower portion is concave.

*Color.*—Juvenile prickles: Greyed-Purple Group 184A. Mature prickles: Greyed-Purple Group 184A.

Plant foliage:

*Compound leaf.*—75 mm (l)×45 (w).

*Quantity.*—3 leaves per 10 cm of stem on average.

*Leaf bearing angle to the stem.*—45 degrees.

*Color of juvenile foliage*.—Upper side: Yellow-Green Group 146A with anthocyanin at the margins the color of Greyed-Purple Group 184A. Lower side: Yellow-Green Group 146B.

*Color of mature foliage*.—Upper side: Yellow-Green Group 146A. Lower side: Yellow-Green Group 146B.

Plant leaves and leaflets:

*Stipules*.—Size: 12 mm long, mm wide. Quantity: 2 per compound leaf. Shape: Linear, slightly broad based with outward extending apices. Margins: Finely serrated. Color: Yellow-Green Group 146B.

*Petiole*.—Length: 15 mm. Diameter: 2 mm. Upper surface: Color: Yellow-Green Group 144B and Greyed-Purple Group 183B. Lower surface: Color: Yellow-Green Group 144A.

*Rachis*.—Length: 25 mm. Upper surface: Color: Yellow-Green Group 144B and Greyed-Purple Group 183B. Lower surface: Color: Yellow-Green Group 144A. Observations: Small prickles Greyed-Red Group 182A.

*Leaflet*.—Quantity: Normally 7 leaflets. Margins: Serrated. Size: On average terminal leaflets are 26 mm long, 15 mm wide. Shape: Generally elliptical. Base: Rounded. Apex: Cuspidate. Texture: Smooth. Thickness: Average. Arrangement: Odd pinnate. Venation: Reticulate. Glossiness: Glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Ground Cover rose class named 'Poultc019', substantially as illustrated and described herein, due to its abundant orange red flowers, disease resistance, and extended period of bloom.

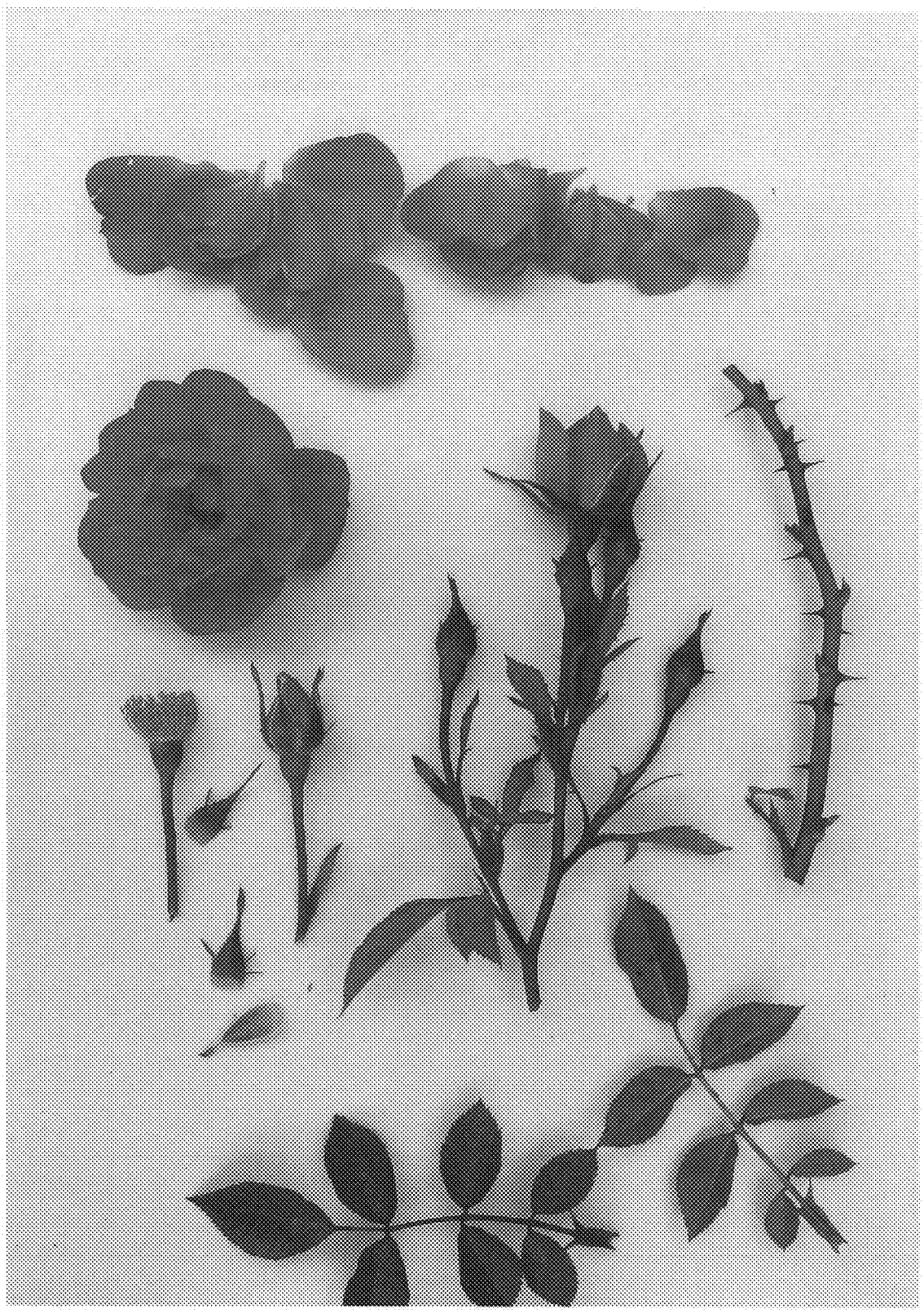

* * * * *